(12) United States Patent
Abbruscato (10) Patent No.: US 9,185,496 B1
(45) Date of Patent: *Nov. 10, 2015

(54) PIEZO ELEMENT STETHOSCOPE (71) Applicant: Charles Richard Abbruscato, Viera, FL (US)

(72) Inventor: Charles Richard Abbruscato, Viera, FL (US)

(*) Notice: Subject to any disclaimer, the term of this patent is extended or adjusted under 35 U.S.C. 154(b) by 338 days.

This patent is subject to a terminal disclaimer.

(21) Appl. No.: 13/764,027

(22) Filed: Feb. 11, 2013

Related U.S. Application Data (63) Continuation-in-part of application No. 12/787,783, filed on May 26, 2010, now Pat. No. 8,447,043, which is a continuation-in-part of application No. 12/590,362, filed on Nov. 6, 2009, now Pat. No. 8,320,576.

(51) Int. Cl.
*H04R 17/02* (2006.01)
(52) U.S. Cl.
CPC ........................ *H04R 17/02* (2013.01)
(58) Field of Classification Search
USPC ............... 381/67, 190; 600/528, 586
See application file for complete search history.

(56) References Cited

U.S. PATENT DOCUMENTS

| | | | |
|---|---|---|---|
| 4,535,205 A | 8/1985 | Ravinet et al. | |
| 4,784,154 A | 11/1988 | Shirley et al. | |
| 5,022,405 A | 6/1991 | Hok et al. | |
| 5,131,400 A | 7/1992 | Harada et al. | |
| 5,195,142 A | 3/1993 | D'Avolio et al. | |
| 5,238,000 A | 8/1993 | Niwa | |
| 5,283,835 A | 2/1994 | Athanas | |
| 5,284,150 A | 2/1994 | Butterfield et al. | |
| 5,467,771 A | 11/1995 | Narimatsu et al. | |
| 5,551,437 A | 9/1996 | Lotscher | |
| 5,908,027 A | 6/1999 | Butterfield et al. | |
| 5,932,849 A | 8/1999 | Dieken | |
| 6,002,777 A | 12/1999 | Grasfield et al. | |
| 6,159,166 A | 12/2000 | Chesney et al. | |

(Continued)

OTHER PUBLICATIONS

Non-Final Office Action, U.S. Appl. No. 12/590,362, Jun. 7, 2012.

(Continued)

*Primary Examiner* — Duc Nguyen
*Assistant Examiner* — Phan Le
(74) *Attorney, Agent, or Firm* — Miller Patent Services; Jerry A. Miller (57) ABSTRACT

A stethoscope chest piece has a chest piece housing containing a piezoelectric (piezo) element mounted within a housing. The piezo element converts body signals to an electrical representation that is processed by circuitry on a circuit board. A back stop is affixed to the circuit board to prevent excess excursion by the piezo element and may be one of the circuit elements on the circuit board. The circuitry includes a USB interface for passing the electrical representation to a receiving device such as a personal computer. This abstract is not to be considered limiting, since other embodiments may deviate from the features described in this abstract.

20 Claims, 4 Drawing Sheets

(56) References Cited

U.S. PATENT DOCUMENTS

| | | |
|---|---|---|
| 6,491,647 B1 * | 12/2002 | Bridger et al. .............. 600/585 |
| 6,498,854 B1 | 12/2002 | Smith |
| 6,661,897 B2 | 12/2003 | Smith |
| 6,937,736 B2 | 8/2005 | Toda |
| 8,320,576 B1 | 11/2012 | Abbruscato |
| 2005/0058298 A1 | 3/2005 | Smith |
| 2005/0157888 A1 | 7/2005 | Yang |
| 2007/0106179 A1 | 5/2007 | Bagha et al. |
| 2007/0165872 A1 * | 7/2007 | Bridger et al. .............. 381/67 |
| 2009/0060215 A1 * | 3/2009 | Ocasio .............. 381/67 |
| 2009/0211838 A1 | 8/2009 | Bilan |

OTHER PUBLICATIONS

Non-Final Office Action, U.S. Appl. No. 12/787,783, Dec. 20, 2012.

* cited by examiner

PIEZO ELEMENT STETHOSCOPE

CROSS REFERENCE TO RELATED APPLICATIONS

This application is a continuation-in-part of application Ser. No. 12/787,783 filed May 26, 2010 which is a continuation-in-part of application Ser. No. 12/590,362 filed Nov. 6, 2009 entitled Piezo Element Stethoscope to Abbruscato both of which are hereby incorporated by reference.

COPYRIGHT AND TRADEMARK NOTICE

A portion of the disclosure of this patent document contains material which is subject to copyright protection. The copyright owner has no objection to the facsimile reproduction of the patent document or the patent disclosure, as it appears in the Patent and Trademark Office patent file or records, but otherwise reserves all copyright rights whatsoever. Trademarks are the property of their respective owners.

BACKGROUND

Traditional stethoscopes pick up signals generated within the body with a chest piece head and deliver them as an acoustic signal to an ear piece via a tube for the clinician to hear. The most common type of electronic stethoscopes use a chest piece head to convert the body's sounds to acoustic, then use microphones to convert the acoustic signal to an analog electrical signal. The analog electrical signal can be processed with analog filters and amplifiers or converted to digital format and processed with digital signal processing techniques.

Another type of electronic stethoscopes uses a piezo (piezoelectric) element to directly convert the internal body signals to analog electrical signals. But using piezo elements creates new challenges. Electronically, a piezo element is modeled as a low impedance voltage source in series with a capacitance. The piezo elements currently in use have a very small equivalent capacitance. This is an important consideration when coupling the piezo element to an amplifier to boost the signal so that it can be heard by the clinician. Unless the amplifier accounts for and compensates for the effects of the series capacitance, the frequency response of the body signal can be altered.

In practice, the capacitance of a coupling cable is significant enough in relation to the capacitance of the piezo element, that it adversely affects the frequency response of the body signal. To avoid the distortions to the signal this could cause, the current state of the art is to put an electronic buffer amplifier in the same housing as the piezo element. The input capacitance of the buffer amplifier is very low and its input impedance is very high, thus preserving the fidelity of the signal from the piezo element. The output impedance of the buffer amplifier is low and relatively immune to the characteristics of the load, including the capacitance and inductance of a filter or cable. The current state of the art for electronic stethoscopes using piezo elements for the pickup sensor requires that a buffer amplifier be co-located in the same housing with the piezo element.

However, by housing the buffer amplifier and the piezo element together, sanitizing the chest piece assembly becomes problematic. Unless the housing assembly is sealed against moisture and liquids, the buffer amplifier electronic components could become damaged while in an autoclave or other liquid sanitizing cleaning method. Sealing the housing with the piezo element and buffer amplifier such that the sensor operation of the piezo element is not adversely affected is difficult and expensive. Therefore, to be competitive in the market, the housing is not perfectly sealed. As a result, these piezo element based electronic stethoscopes are not used in a surgical environment where sanitizing or sterilizing is required. However, in some environments, collocation of the buffer amplifier and other circuitry within the chest-piece can be advantageous.

In addition, in some environments it would be advantageous to have a universal serial bus (USB) interface to provide for control from the receiving device to which the chest piece assembly is connected. Further, other circuitry could be included in the chest piece assembly to allow adjusting the gain of the amplifier and signal processing such as filters and encoding options under control of the receiving device.

BRIEF DESCRIPTION OF THE DRAWINGS

Certain illustrative embodiments illustrating organization and method of operation, together with objects and advantages may be best understood by reference detailed description that follows taken in conjunction with the accompanying drawings in which.

DETAILED DESCRIPTION

While this invention is susceptible of embodiment in many different forms, there is shown in the drawings and will herein be described in detail specific embodiments, with the understanding that the present disclosure of such embodiments is to be considered as an example of the principles and not intended to limit the invention to the specific embodiments shown and described. In the description below, like reference numerals are used to describe the same, similar or corresponding parts in the several views of the drawings.

The terms "a" or "an", as used herein, are defined as one or more than one. The term "plurality", as used herein, is defined as two or more than two. The term "another", as used herein, is defined as at least a second or more. The terms "including" and/or "having", as used herein, are defined as comprising (i.e., open language). The term "coupled", as used herein, is defined as connected, although not necessarily directly, and not necessarily mechanically.

Reference throughout this document to "one embodiment", "certain embodiments", "an embodiment", "an example", "an implementation" or similar terms means that a particular feature, structure, or characteristic described in connection with the embodiment, example or implementation is included in at least one embodiment, example or implementation of the present invention. Thus, the appearances of such phrases or in various places throughout this specification are not necessarily all referring to the same embodiment, example or implementation. Furthermore, the particular features, structures, or characteristics may be combined in any suitable manner in one or more embodiments, examples or implementations without limitation.

The term "or" as used herein is to be interpreted as an inclusive or meaning any one or any combination. Therefore, "A, B or C" means "any of the following: A; B; C; A and B; A and C; B and C; A, B and C". An exception to this definition will occur only when a combination of elements, functions, steps or acts are in some way inherently mutually exclusive.

A stethoscope utilizing a piezo element in a manner consistent with embodiments of the present invention places the piezo element for the chest piece sensor in a simple housing with novel features. A low cost, rugged, passive piezo element is used as the pickup sensor such that no electronics are used in the chest piece. This allows it to be cleaned in a steam autoclave or other sanitizing or sterilizing method without risk of damaging the chest piece. In other embodiments, co-location of electronics within the chest-piece housing can also be accomplished. In each case, a backstop can be utilized as described below to reduce the risk of damage to the piezo element.

In certain example embodiments, the piezo element is a metal, such as brass or stainless steel. The housing comes in two pieces—a Top Piece and Bottom Piece. The Top Piece is metal, preferably stainless steel, and clamps the piezo element around its rim against the Bottom Piece The Top Piece has a special internal protrusion to serve as a stop behind the piezo element to prevent it from over flexing, thus making it very rugged.

The Top Piece of the chest piece is made from a non-corroding metal such as stainless steel, which is not damaged or degraded in an autoclave or other sanitizing or sterilizing method. In addition, the metal housing provides a weight or mass that works against the piezo element to improve the performance of the piezo element and reduce extraneous pickup of noise from the user holding the chest piece.

In accord with certain implementations, a low cost piezo based chest piece need not contain active electronic elements and batteries and requires no external power source to function. The chest piece head has features to make it rugged and has significant mass to improve performance. The chest piece is detachable from the electronic stethoscope and can be sanitized or sterilized separate from the electronics module, thus allowing its use in a surgical environment.

Figure 1:
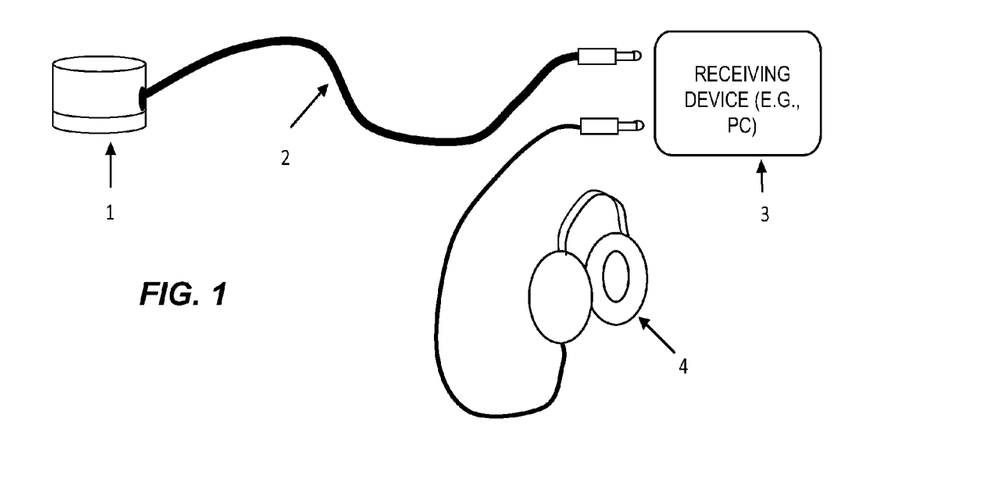
FIG. 1 is an example of a complete stethoscope system consistent with certain embodiments of the present invention.

FIG. 1 shows the complete stethoscope system with the chest piece 1, the coupling cable 2, the electronics module 3, and the headset 4. The chest piece 1 senses the body signals and converts them to electrical analog signals, which are sent over the cable to the electronics module 3. Electronics module 3 amplifies the signal and may carry out other signal processing functions. Many variations on this can be devised. For example, the cable 2 can be attached to the chest piece 1 or plug into the chest piece 1 at one end and plug into the electronics module 3 at the other end. Other audio or visual signal processing and/or reproduction can be used in place of headphones 4. Either way, the chest piece 1 can preferably be removed and sanitized or sterilized separately from the electronics module.

The electronics module 3 contains the amplifiers and filters and other components to provide the audible signal representing the body sounds to the clinician listening on the headset. The listening means can be a headset, an ear bud type listening device, loudspeaker or any convenient means of listening to the audio signal. Other implementations may also record or provide a visual display of the signal from the chest piece 1.

Figure 2:
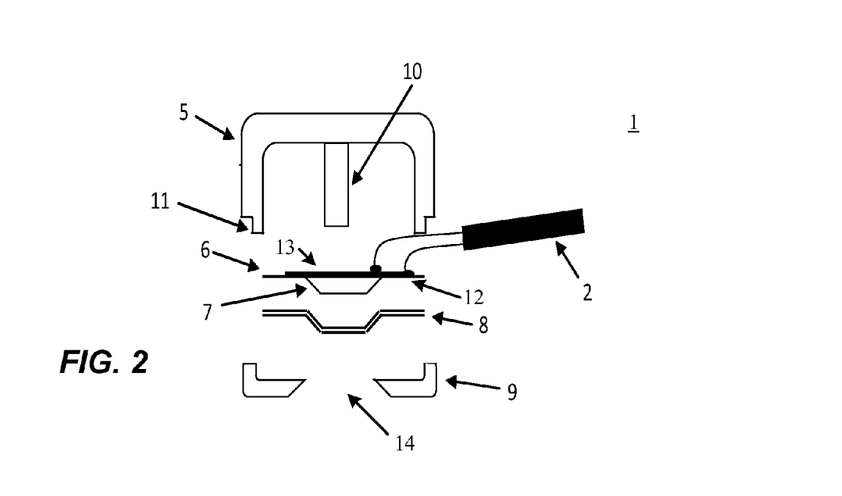
FIG. 2 is a diagram depicting an example of a chest piece implementation for a stethoscope consistent with certain embodiments of the present invention.

FIG. 2 shows the construction of an example implementation of the chest piece 1 in cross section. The core of the chest piece 1 is a piezoelectric element sensor 6 with a suitable structure to hold the piezo element sensor 6 in place and a set of wires 2 attached to the two electrical contacts of the piezo sensor 6 to convey the signals that it picks up. The piezo sensor element 6 may be made up of a round metal plate 12, for example brass or stainless steel, with a ceramic (or other piezoelectric material) disk 13 of smaller diameter than the metal plate 12 attached to one side. The signal generated by the piezo element 6 is a voltage potential between the ceramic disk 13 and the metal plate 12 as a result of the piezoelectric effect. While a disk shape is preferred and used as an illustrative example herein, the ceramic or other piezoelectric layer can be of any suitable geometry (square, oval, rectangular, etc).

The bottom piece 9 of the chest piece 1 has a hole 14 in the middle of its bottom face. The piezo element 6 has a plastic or rubber button 7 adhered to its metal plate 12 side and two wires in a cable 2 attached (typically soldered or welded) to the top side where the ceramic disk 13—one wire to the ceramic element 13 and one wire to the metal plate 12. The piezo element 6 is placed inside the bottom piece 9 so that the button 7 protrudes into the opening in the face of the bottom piece 9. Pressure signals on the button 7 are conveyed to the piezo element 6 and converted to electrical signals that are in turn conveyed via the wires of cable 2. A Silicone cover 8 is placed over the piezo element 6 with button 7 attached to provide an inert material for the surface that would touch the patient. The top piece 5 has its bottom rim 11 shaped so that it fits inside the bottom piece and clamps down on the outside rim of the piezo element 6 to the bottom piece 9. A hole or slot is cut in the top piece 5 for the cable 2 to pass through.

Using a metal top piece 5 to clamp the outside rim of the piezo element 6 firmly against the bottom piece 9 maximizes the performance of the piezo element 6. The relatively heavy mass of the metal top piece 5 inhibits the vibration from the piezo element 6 from being dissipated by the metal shell comprised of the top piece 5 and the bottom piece 9 and channels the maximum vibration to the ceramic disk 13 of the piezo element 6, thus generating the maximum signal. The top piece 5 is designed to have relatively high mass of about 12 grams to inhibit vibration. A top piece 5 mass of about 9-20 grams is currently preferred.

There is a post or protrusion 10 inside the top piece 5 that extends nearly to the piezo element 6. The post or protrusion 10 provides a backstop for the piezo element 6 so that it cannot flex excessively and be damaged. Without post or protrusion 10, the piezo element 6 could be damaged by pressing hard on the button 7. The post or protrusion 10 serves as a "backstop" and can be secured to top piece 5 or could be molded to be an integral part of top piece 5. In one preferred implementation, the protrusion 10 rests approximately 0.6 mm from the top of the ceramic disk 13 of the piezo element 6 when fully assembled in order to limit the excursion of the piezo element. The exact distance or range of distance is somewhat dependent upon the actual piezo element 6 used. The distance can be smaller up to the point where the ceramic disk 13 nearly touches the protrusion 10. The distance can be larger but if it gets too large for a selected piezo element 6, then the protrusion 10 would not prevent damage to the piezo element 6. Hence, the protrusion 10 should be spaced far enough away from the piezo element 6 so as not to interfere with the movement of the piezo element 6, but should be close enough to stop its movement beyond a point where the piezo element 6 would incur damage from further movement. For piezo elements of the size used herein, a gap of approximately 0.5-0.7 mm is suitable and preferably about 0.6 mm.

The piezo element with a metal plate has a relatively large series capacitance and is capable of generating a relatively large analog electrical signal with the chest piece assembly 1 described. By selecting a piezo element with a series capacitance that is a at least 1-2 orders of magnitude greater than the distributed capacitance of a connecting cable plus the input capacitance of the buffer amplifier, the buffer amplifier module 3 can be implemented separately connected by an inexpensive audio cable without introducing discernible distortion and noise. For one simple inexpensive implementation with a satisfactorily large capacitance, the piezo element 6 is approximately 0.23 mm thick and approximately 27 mm in diameter resulting in over 570 $mm^2$ of surface area and a series capacitance of the piezo element 6 of between 10,000 pF-40,000 pF. The distributed capacitance of the cable 3, which may be an inexpensive 2 meter audio cable (unbalanced audio cable typically has a capacitance of 200 pf per meter), plus the amplifier input capacitance (typically in the range of 30 pF) is approximately 430 pF resulting in no discernable distortion in the presently preferred implementation. The buffer amplifier is constructed using a conventional commercially available operational amplifier, and the cable 3 is a two conductor shielded audio cable approximately 2-3 meters long. All the elements in the chest piece, when constructed as described, can be sanitized in an autoclave or liquid sanitizing solution without damage. Many variations will occur to those skilled in the art.

Hence, a stethoscope chest piece consistent with certain implementations uses a piezo element as the sensor to pick up body sounds, where the piezo element is passive, is made from an inert or stable metal, there are no active electronic components in the chest piece, all components of the chest piece are inert or stable such that they are not damaged if they are sanitized in an autoclave or liquid sanitizing solution and no special sealing is required to prevent damage if the chest piece is sanitized in an autoclave or liquid sanitizing solution.

Certain implementations use a piezo element that is relatively large (e.g. about 27 mm in diameter) and thereby yields a relatively large equivalent capacitance (e.g. 10,000 pF-40,000 pF) so that the output of the piezo element can be coupled to an external amplifier module with an ordinary inexpensive audio cable. The chest piece enclosure material that is not only inert or stable, but is relatively heavy to maximize the performance of the piezo element and minimize extraneous noise due to handling the chest piece is preferred. A post or protrusion is provided inside the metal chest piece top to provide a backstop to the piezo element to prevent it from being damaged by over flexing.

Combining the above concepts yields a chest piece with high performance, high fidelity, and is easier and less expensive to manufacture than the current state of the art stethoscope implementations incorporating piezo elements.

As previously noted, when housing a buffer amplifier and the piezo element together, sanitizing the chest piece assembly becomes problematic. Unless the housing assembly is sealed against moisture and liquids, the buffer amplifier electronic components could become damaged while in an autoclave or other liquid sanitizing cleaning method. Sealing the housing with the piezo element and buffer amplifier such that the sensor operation of the piezo element is not adversely affected is difficult and expensive. Therefore, to be competitive in the market, the housing is not perfectly sealed. As a result, these piezo element based electronic stethoscopes may be more difficult to use in a surgical environment where sanitizing or sterilizing is required. However, it may be desirable in some circumstances to utilize a chest piece with an integral buffer amplifier or other integral circuit, whether sealed or unsealed, without limitation.

Piezo elements (PE) used with stethoscopes have commonly been constructed from various film material. There are some inherent differences between PEs constructed from film materials versus those made with a metal plate. This starts with structural strength; a metal based PE can be made much larger than a film based PE.

The larger size is inherently more sensitive in general, with even greater sensitivity for lower frequency signals. Further, the larger size results in a greater equivalent series capacitance. When the capacitance is significantly larger than the distributed capacitance of a coupling cable, then the signal from the PE can be coupled to a separate amplifier with minimal distortion. This avoids the requirement for having an amplifier in the same housing as the PE and offers general benefits to a broad base of users.

However, as previously noted, there are some cases where having an amplifier in the same housing as the PE offers an advantage. Specifically, where it is desirable to have a signal from the chest piece assembly to be similar in level to an equivalent chest piece assembly that uses an electret microphone as the transducer, which itself includes an integral amplifier. While having an integral amplifier adds cost the PE based chest piece assembly, for cases where it has to emulate a microphone type chest piece assembly, such cost can often be justified.

Hence, there are cases where a PE based chest piece assembly with an integral amplifier can benefit from the superior low frequency response of a PE made with a metal plate. Having a printed circuit board (PCB) embedded in the chest piece assembly is a physical challenge. Moreover, in accord with the present teachings, a backstop is provided to provide for the benefits described above. Thus, manufacturing a chest piece assembly is made more difficult with the use of a backstop to provide support for the PE.

In this implementation, at least one component on the integral PCB is placed behind the PE to provide the function of a backstop, thus eliminating the need for a separate backstop post. Such component may either serve the sole function of serving as a backstop, or may be embodied as a strategically placed electronic component that can serve the dual purpose of providing a backstop. For example, an amplifier chip or electrolytic capacitor of suitable height can be strategically situated and can serve as the backstop.

Hence in one embodiment, by knowing the thickness of the PCB and the height of the tallest component mounted on the PCB, the PCB can be mounted inside the chest piece assembly such that the spacing between the top of that component and the PE is the same as the spacing between the backstop post and the PE in the implementation described above, and in any event, positioned at a point that prevents excessive excursions of the PE such that the PE could be more readily damaged.

The Printed Circuit Board Assembly (PCBA) in the chest piece assembly provides the amplifier circuitry to bring the signal level from the PE up to the approximate level that would come from an electret microphone, or other desired level. Just as an electret microphone gets its operating voltage from the Microphone input port, so does the circuitry situated on the PCB such as an amplifier. An example block diagram for the circuitry of an example PCBA is shown in the FIG. 3.

Figure 3:
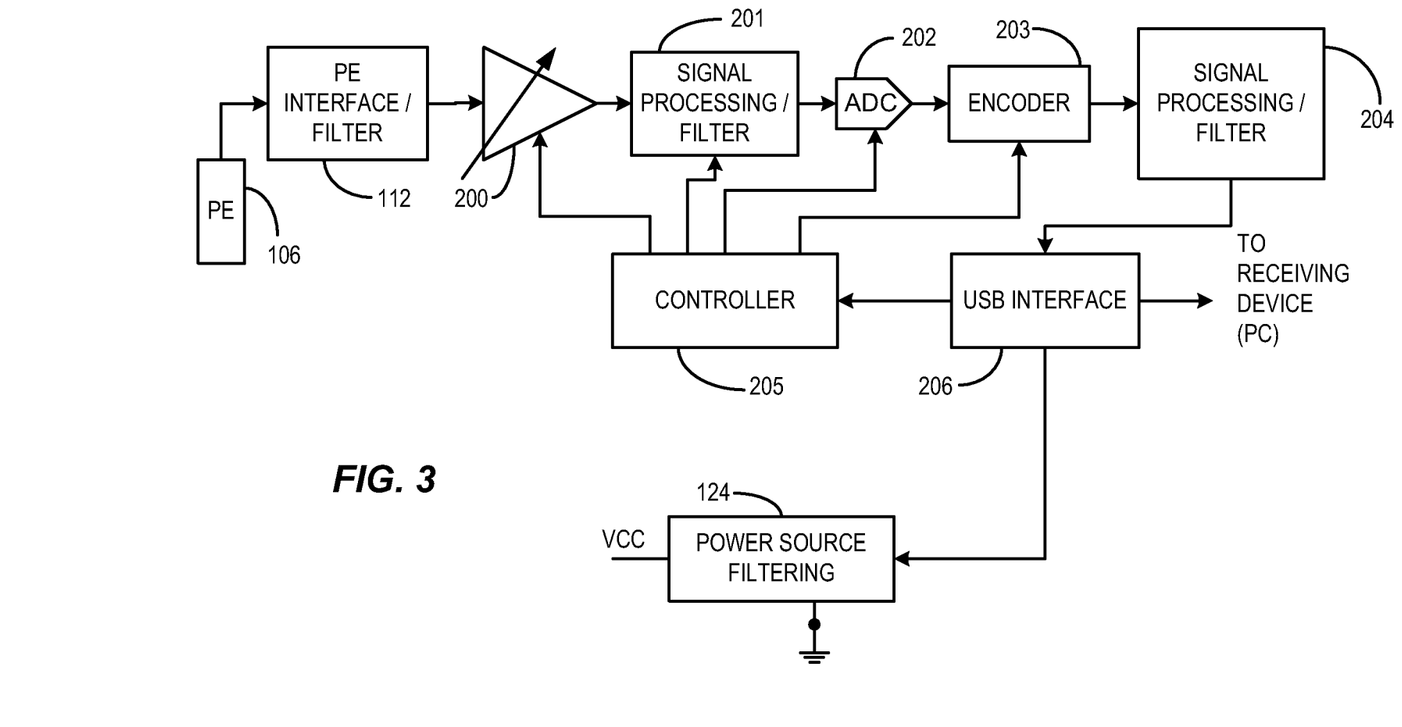
FIG. 3 depicts an example block diagram of a circuit used in an active chest piece consistent with certain embodiments of the present invention.

In this example of FIG. 3, an amplifier 200 is provided to amplify the signal produced by the PE element 106. Amplifier 200 may be a variable gain amplifier in certain implementations. There may be other circuitry before amplifier 200 such as 112 to provide impedance matching, filtering, interfacing, and/or protection from external transients. Additionally, the PCB circuit may be provided with power source filtering circuitry 124 for stability of the amplifier and to avoid noise problems.

The output of the chest piece assembly includes a bi-directional USB interface 206 that allows transmission of stethoscope signal data to the receiving device 3 and accepts control signal data from the receiving device 3.

The output of amplifier 200 goes to optional signal processing circuitry such as a filter 201. From there the signal is converted from analog format to digital format with an analog to digital converter (ADC) 202. The digitized signal from ADC 202 is then formatted by an encoder 203. In certain example implementations, the formatting can be Linear pulse code modulation (PCM), but this is not to be considered limiting since other formats of encoding could also be used. The digitally formatted signal may be filtered at 204 or be subjected to some other signal processing before being fed to the USB interface 206 where it is transformed to the USB communications standard format. The USB interface is bidirectional and can pass control information to controller 205 to adjust the gain of amplifier 200, or change the filters of 201 and 204, or change encoding formats of 203, for example.

Figure 4:
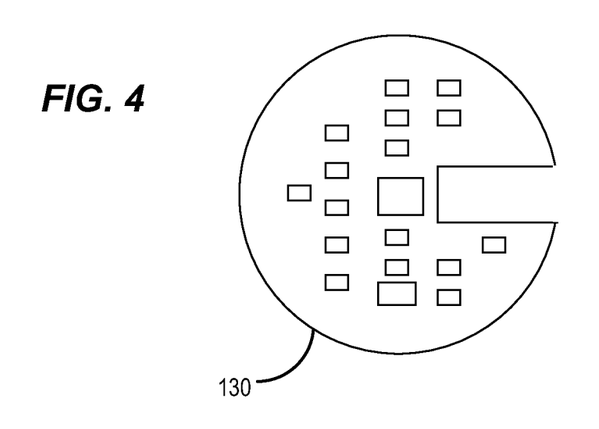
FIG. 4 depicts a top view of an example circuit board used in an active chest piece consistent with certain embodiments of the present invention.
Figure 5:
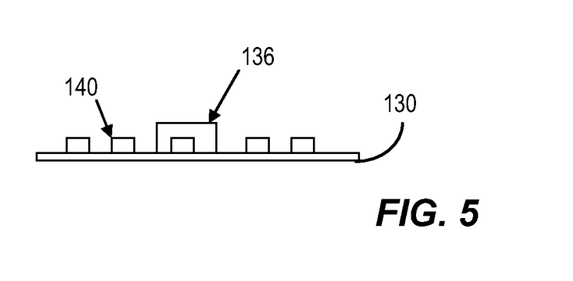
FIG. 5 depicts a side view of an example circuit board used in an active chest piece consistent with certain embodiments of the present invention.

In this implementation, the circuitry is placed on a printed circuit board (PCB) that may have a round shape, approximately round shape, or other suitable shape to readily fit into the chest piece housing as shown in a top view in FIG. 4. When viewed from the side as shown in FIG. 5, it will be noted that components of various heights can be present on the PCB. For example, the tallest component 136 is preferably, but not necessarily, mounted centrally with supporting components mounted thereabouts such as component 140. As previously mentioned, the component 136 can be either an electrical component mounted strategically to serve as a back stop, or if room permits, a separate component can be mounted there to serve solely as a backstop.

The PCBA 130 can be mounted inside the chest piece assembly so that the tallest component on the PCBA is positioned the desired distance from the PE to serve the backstop function to prevent the PE from being damaged if pushed in by a user or otherwise exposed to extreme excursions.

Figure 6:
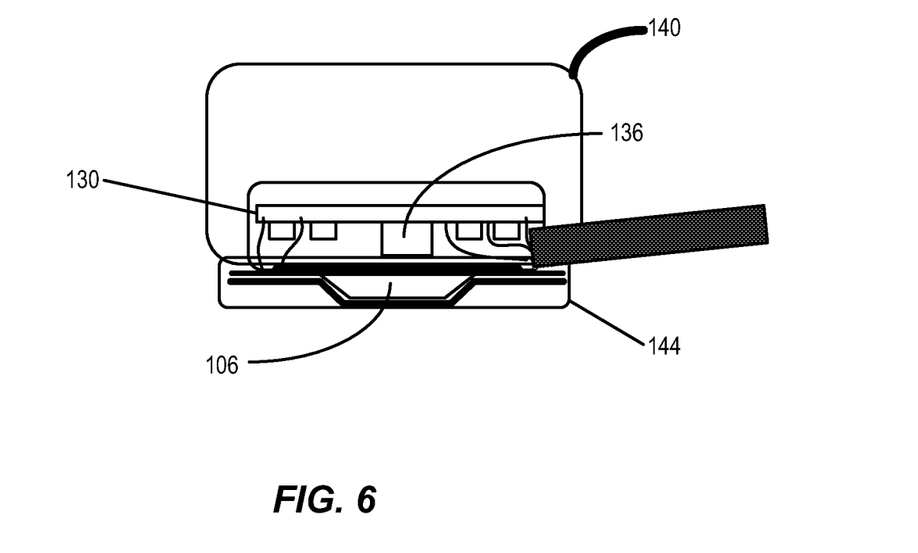
FIG. 6 depicts a cross sectional view of an example active chest piece assembly consistent with certain embodiments of the present invention.

FIG. 6 shows a cross-section of a physical representation of chest piece assembly with a tall component 136 on a PCBA 130 providing the backstop function for the PE 106 mounted below it. The assembly is enclosed within an enclosure top 140 and an enclosure bottom 144.

Thus, in certain implementations of a passive stethoscope chest piece, the chest piece has a chest piece housing containing a piezoelectric (piezo) element mounted within a housing. The piezo element converts body signals to an electrical representation that is processed by circuitry on a circuit board. A back stop is affixed to the circuit board to prevent excess excursion by the piezo element and may be one of the circuit elements on the circuit board.

Thus, in certain implementations, a passive stethoscope chest piece has a chest piece housing containing: a passive piezoelectric (piezo) element having a piezoelectric layer (such as a ceramic disk) and a metal layer (preferably a disk); a pair of electrical connections to the piezo element so that the piezo element serves to pick up body sounds and provide an electrical representation of the body sounds to the electrical connections and pass the electrical representation outside the housing for processing by external circuitry; and where the housing includes a backstop comprising a post affixed to the housing and protruding toward a central area of the piezo element.

In certain implementations, no active electronic components are disposed within the housing. In certain implementations, the housing and metal plate are made from an inert or stable metal that can be sanitized in an autoclave or liquid sanitizing solution without degradation of operation. In certain implementations, the housing is unsealed. In certain implementations, the piezo element has approximately 570 mm squared of surface area. In certain implementations, the piezo element has series capacitance of at least 10,000 pF. In certain implementations, the electrical connectors connect to a cable and an external circuit, and where the capacitance of the piezo element is at least ten times the combined capacitance of the cable and external circuit. In certain implementations, the back stop is situated so as to prevent the piezo element from flexing beyond a point that would damage the piezo element. In certain implementations, the back stop is situated approximately 5-7 mm from a center of the piezo element.

Another passive stethoscope chest piece has a chest piece housing containing: a passive piezoelectric (piezo) element; a pair of electrical connections to the piezo element so that the piezo element serves to pick up body sounds and provide an electrical representation of the body sounds to the electrical connections and pass the electrical representation outside the housing for processing by external circuitry; where no active electronic components are disposed within the housing; and the housing having a back stop situated so as to prevent the piezo element from flexing beyond a point that would damage the piezo element.

In certain implementations, the housing and metal plate are made from an inert or stable metal that can be sanitized in an autoclave or liquid sanitizing solution without degradation of operation. In certain implementations, the housing is unsealed. In certain implementations, the piezo element is approximately 570 mm square in surface area. In certain implementations, the piezo element has series capacitance of at least 10,000 pF. In certain implementations, the piezo element has a series capacitance of between 10,000 pF and 40,000 pF. In certain implementations, the electrical connectors connect to a cable and an external circuit, and where the capacitance of the piezo element is at least ten times the combined capacitance of the cable and external circuit. In certain implementations, the back stop is situated approximately 5-7 mm from a center of the piezo element. In certain implementations, the backstop comprises a post affixed to the housing and protruding toward a central area of the piezo element.

Another passive stethoscope chest piece consistent with certain implementations has an unsealed chest piece housing, where the housing and metal plate are made from an inert or stable metal that can be sanitized in an autoclave or liquid sanitizing solution without degradation of operation, the housing containing. A passive piezoelectric (piezo) element has at least 10,000 pF in series capacitance. A pair of electrical connections to the metal plate and ceramic disk of the piezo element so that the piezo element serves to pick up body sounds and provides an electrical representation of the body sounds to the electrical connections and pass the electrical representation outside the housing for processing by external circuitry, where no active electronic components are disposed within the housing. The electrical connectors connect to a cable and an external circuit, and where the capacitance of the piezo element is at least ten times the combined capacitance of the cable and external circuit. A post is affixed to the housing and forming a back stop situated approximately 5-7 mm from a central area of the piezo element so as to prevent the piezo element from flexing beyond a point that would damage the piezo element. In certain implementations, the post is integral to a portion of the housing.

Thus, in another implementation, an active stethoscope chest piece has a chest piece housing containing: a piezoelectric (piezo) element situated so as to pick up body sounds and provides an electrical representation of the body sounds to electrical connections; a printed circuit board carrying electronic components and connected to the electrical connections which processes the electrical representation of the body sounds and passes the processed electrical representation outside the housing for processing by external circuitry. The printed circuit board includes a backstop protruding toward a central area of the piezo element.

In certain implementations, the backstop comprises an electrical component mounted to the printed circuit board and serving both as a circuit element and as a backstop. In certain implementations, the housing and metal plate are made from an inert or stable metal. In certain implementations, the piezo element has series capacitance of at least 10,000 pF. In certain implementations, the printed circuit board is connected to a cable and an external circuit. In certain implementations, the back stop is situated so as to prevent the piezo element from flexing beyond a point that would damage the piezo element. In certain implementations, the back stop is situated approximately 0.5-0.7 mm from a center of the piezo element. In certain implementations, the printed circuit board carries an amplifier circuit. In certain implementations, the back stop comprises a tallest component situated on the printed circuit board.

In another active stethoscope chest piece, a chest piece housing contains: a piezoelectric (piezo) element situated so as to pick up body sounds and provides an electrical representation of the body sounds to electrical connections; a printed circuit board carrying electronic components and connected to the electrical connections which processes the electrical representation of the body sounds and passes the processed electrical representation outside the housing for processing by external circuitry. The printed circuit board includes a backstop protruding toward a central area of the piezo element, and where the backstop comprises an electrical component mounted to the printed circuit board and serving both as a circuit element and as a backstop.

In certain implementations, the housing and metal plate are made from an inert or stable metal. In certain implementations, the piezo element has series capacitance of at least 10,000 pF. In certain implementations, the printed circuit board is connected to a cable and an external circuit. In certain implementations, the back stop is situated so as to prevent the piezo element from flexing beyond a point that would damage the piezo element. In certain implementations, the back stop is situated approximately 0.5-0.7 mm from a center of the piezo element. In certain implementations, the printed circuit board carries an amplifier circuit. In certain implementations, the back stop comprises a tallest component situated on the printed circuit board.

In another implementation, an active stethoscope chest piece has a chest piece housing containing: a piezoelectric (piezo) element situated so as to pick up body sounds and provides an electrical representation of the body sounds to electrical connections, where the piezo element has series capacitance of at least 10,000 pF; and a printed circuit board carrying electronic components and connected to the electrical connections which processes the electrical representation of the body sounds and passes the processed electrical representation outside the housing for processing by external circuitry. The printed circuit board includes a backstop protruding toward a central area of the piezo element, and where the backstop comprises an electrical component that is taller than other electrical components mounted to the printed circuit board, the electrical component serving both as a circuit element and as a backstop, where the back stop is situated so as to prevent the piezo element from flexing beyond a point that would damage the piezo element and is approximately 5-7 mm from a center of the piezo element, and the printed circuit board is connected to a cable and an external circuit. In certain implementations, the printed circuit board carries an amplifier circuit.

In certain implementations, an active stethoscope chest piece has a chest piece housing containing a piezoelectric (piezo) element situated so as to pick up body sounds and provides an electrical representation of the body sounds to electrical connections; a circuit board carrying electronic components and connected to the electrical connections which processes the electrical representation of the body sounds; a universal serial bus (USB) interface receiving a digitized version of the electrical representation of the body sounds and configured to pass the digitized version of the processed electrical representation outside of the housing. The circuit board includes a backstop protruding toward a central area of the piezo element, and where the back stop is situated so as to prevent the piezo element from flexing beyond a point that would damage the piezo element.

In certain implementations, the backstop is an electrical component mounted to the circuit board and serving both as a circuit element and as a backstop. In certain implementations, the USB interface comprises a bidirectional interface that receives control signals from a device external to the housing that controls circuits residing on the circuit board. In certain implementations, the circuit board carries an amplifier circuit that is controlled by the device external to the housing via the USB interface. In certain implementations, the circuit board carries a filter circuit that is controlled by the device external to the housing via the USB interface. In certain implementations, the circuit board carries a signal processor circuit that is controlled by the device external to the housing via the USB interface. In certain implementations, the circuit board carries an encoder that is controlled by the device external to the housing via the USB interface to select a digital data encoding format for encoding the digitized version of the electrical representation of the body sounds. In certain implementations, the back stop comprises a tallest component situated on the circuit board.

Another active stethoscope chest piece has a chest piece housing containing: a piezoelectric (piezo) element situated so as to pick up body sounds and provides an electrical representation of the body sounds to electrical connections; a circuit board carrying electronic components and connected to the electrical connections which processes the electrical representation of the body sounds; and a universal serial bus (USB) interface receiving a digitized version of the electrical representation of the body sounds and configured to pass the digitized version of the processed electrical representation outside of the housing. The circuit board includes a backstop protruding toward a central area of the piezo element, and the backstop comprises an electrical component mounted to the circuit board and serving both as a circuit element and as a backstop, and the back stop is situated so as to prevent the piezo element from flexing beyond a point that would damage the piezo element.

In certain implementations, the USB interface comprises a bidirectional interface that receives control signals from a device external to the housing that controls circuits residing on the circuit board. In certain implementations, the circuit board carries an amplifier circuit that is controlled by the device external to the housing via the USB interface. In certain implementations, the circuit board carries a filter circuit that is controlled by the device external to the housing via the USB interface. In certain implementations, the circuit board carries a signal processor circuit that is controlled by the device external to the housing via the USB interface. In certain implementations, the circuit board carries an encoder that is controlled by the device external to the housing via the USB interface to select a digital data encoding format for encoding the digitized version of the electrical representation of the body sounds. In certain implementations, the back stop comprises a tallest component situated on the circuit board.

Another embodiment of an active stethoscope chest piece has a chest piece housing containing: a piezoelectric (piezo) element situated so as to pick up body sounds and provides an electrical representation of the body sounds to electrical connections; and a circuit board carrying electronic components and connected to the electrical connections which processes the electrical representation of the body sounds. The circuit board includes a backstop protruding toward a central area of the piezo element, and the backstop comprises an electrical component that is taller than other electrical components mounted to the circuit board, the electrical component serving both as a circuit element and as a backstop, where the back stop is situated so as to prevent the piezo element from flexing beyond a point that would damage the piezo element and is approximately 0.5-0.7 mm from a center of the piezo element. The USB interface is a bidirectional interface that receives control signals from a device external to the housing that controls circuits residing on the circuit board.

In certain implementations, the circuit board carries an amplifier circuit that is controlled by the device external to the housing via the USB interface. In certain implementations, the circuit board carries a filter circuit that is controlled by the device external to the housing via the USB interface. In certain implementations, the circuit board carries a signal processor circuit that is controlled by the device external to the housing via the USB interface. In certain implementations, the circuit board carries an encoder that is controlled by the device external to the housing via the USB interface to select a digital data encoding format for encoding the digitized version of the electrical representation of the body sounds.

A stethoscope chest piece has a chest piece housing containing a piezoelectric (piezo) element mounted within a housing. The piezo element converts body signals to an electrical representation that is processed by circuitry on a circuit board. A back stop is affixed to the circuit board to prevent excess excursion by the piezo element and may be one of the circuit elements on the circuit board. The circuitry includes a USB interface for passing the electrical representation to a receiving device such as a personal computer.

While certain illustrative embodiments have been described, it is evident that many alternatives, modifications, permutations and variations will become apparent to those skilled in the art in light of the foregoing description.

What is claimed is:

1. An active stethoscope chest piece, comprising:
   a chest piece housing containing:
   a piezoelectric (piezo) element situated so as to pick up body sounds and provide an electrical representation of the body sounds to electrical connections;
   a circuit board carrying electronic components and connected to the electrical connections which processes the electrical representation of the body sounds;
   a universal serial bus (USB) interface receiving a digitized version of the electrical representation of the body sounds and configured to pass the digitized version of the processed electrical representation outside of the housing; and
   where the circuit board includes a backstop protruding toward a central area of the piezo element, and where the back stop is situated so as to prevent the piezo element from flexing beyond a point that would damage the piezo element.

2. The chest piece according to claim 1, where the backstop comprises an electrical component mounted to the circuit board and serving both as a circuit element and as a backstop.

3. The chest piece according to claim 1, where the USB interface comprises a bidirectional interface that receives control signals from a device external to the housing that controls circuits residing on the circuit board.

4. The chest piece according to claim 3, where the circuit board carries an amplifier circuit that is controlled by the device external to the housing via the USB interface.

5. The chest piece according to claim 3, where the circuit board carries a filter circuit that is controlled by the device external to the housing via the USB interface.

6. The chest piece according to claim 3, where the circuit board carries a signal processor circuit that is controlled by the device external to the housing via the USB interface.

7. The chest piece according to claim 3, where the circuit board carries an encoder that is controlled by the device external to the housing via the USB interface to select a digital data encoding format for encoding the digitized version of the electrical representation of the body sounds.

8. The chest piece according to claim 1, where the back stop comprises a tallest component situated on the circuit board.

9. An active stethoscope chest piece, comprising:
   a chest piece housing containing:
   a piezoelectric (piezo) element situated so as to pick up body sounds and provide an electrical representation of the body sounds to electrical connections;
   a circuit board carrying electronic components and connected to the electrical connections which processes the electrical representation of the body sounds;
   a universal serial bus (USB) interface receiving a digitized version of the electrical representation of the body sounds and configured to pass the digitized version of the processed electrical representation outside of the housing; and
   where the circuit board includes a backstop protruding toward a central area of the piezo element, and where the backstop comprises an electrical component mounted to the circuit board and serving both as a circuit element and as a backstop, and where the back stop is situated so as to prevent the piezo element from flexing beyond a point that would damage the piezo element.

10. The chest piece according to claim 9, where the USB interface comprises a bidirectional interface that receives control signals from a device external to the housing that controls circuits residing on the circuit board.

11. The chest piece according to claim 10, where the circuit board carries an amplifier circuit that is controlled by the device external to the housing via the USB interface.

12. The chest piece according to claim 10, where the circuit board carries a filter circuit that is controlled by the device external to the housing via the USB interface.

13. The chest piece according to claim 10, where the circuit board carries a signal processor circuit that is controlled by the device external to the housing via the USB interface.

14. The chest piece according to claim 10, where the circuit board carries an encoder that is controlled by the device external to the housing via the USB interface to select a digital data encoding format for encoding the digitized version of the electrical representation of the body sounds.

15. The chest piece according to claim 10, where the back stop comprises a tallest component situated on the circuit board.

16. An active stethoscope chest piece, comprising:
a chest piece housing containing:
a piezoelectric (piezo) element situated so as to pick up body sounds and provide an electrical representation of the body sounds to electrical connections;
a circuit board carrying electronic components and connected to the electrical connections which processes the electrical representation of the body sounds;
where the circuit board includes a backstop protruding toward a central area of the piezo element, and where the backstop comprises an electrical component that is taller than other electrical components mounted to the circuit board, the electrical component serving both as a circuit element and as a backstop, where the back stop is situated so as to prevent the piezo element from flexing beyond a point that would damage the piezo element and is approximately 0.5-0.7 mm from a center of the piezo element; and
where the USB interface comprises a bidirectional interface that receives control signals from a device external to the housing that controls circuits residing on the circuit board.

17. The chest piece according to claim 16, where the circuit board carries an amplifier circuit that is controlled by the device external to the housing via the USB interface.

18. The chest piece according to claim 16, where the circuit board carries a filter circuit that is controlled by the device external to the housing via the USB interface.

19. The chest piece according to claim 16, where the circuit board carries a signal processor circuit that is controlled by the device external to the housing via the USB interface.

20. The chest piece according to claim 16, where the circuit board carries an encoder that is controlled by the device external to the housing via the USB interface to select a digital data encoding format for encoding the digitized version of the electrical representation of the body sounds.

* * * * *